(12) United States Patent
Parzermair et al.

(10) Patent No.: US 8,900,873 B2
(45) Date of Patent: Dec. 2, 2014

(54) METHOD FOR CONTINUOUSLY DETERMINING THE CONCENTRATION OF AT LEAST ONE CN COMPOUND IN AN AQUEOUS SOLUTION

(75) Inventors: Franz Parzermair, Pilsbach (AT); Leopold Moser, Dorf/Pram (AT); Manfred Naderer, Pierbach (AT)

(73) Assignee: Voestalpine Stahl GmbH, Linz (AT)

( * ) Notice: Subject to any disclaimer, the term of this patent is extended or adjusted under 35 U.S.C. 154(b) by 122 days.

(21) Appl. No.: 13/388,746

(22) PCT Filed: Aug. 3, 2010

(86) PCT No.: PCT/AT2010/000282
§ 371 (c)(1),
(2), (4) Date: Apr. 11, 2012

(87) PCT Pub. No.: WO2011/014898
PCT Pub. Date: Feb. 10, 2011

(65) Prior Publication Data
US 2012/0195795 A1 Aug. 2, 2012

(30) Foreign Application Priority Data
Aug. 3, 2009 (AT) .................................. 1227/2009

(51) Int. Cl.
*G01N 30/04* (2006.01)
*G01N 30/30* (2006.01)
*G01N 33/18* (2006.01)
*G01N 1/40* (2006.01)

(52) U.S. Cl.
CPC ...... *G01N 33/182* (2013.01); *G01N 2001/4066* (2013.01); *G01N 1/4055* (2013.01)
USPC ............... 436/109; 436/43; 422/35; 422/67; 422/68.1; 422/83; 422/305

(58) Field of Classification Search
CPC ................. G01N 2001/4066; G01N 33/0021; G01N 1/4055; C01C 3/02; B01J 7/00; B01J 10/02; B01J 27/26
USPC ............ 436/109, 43; 422/35, 67, 68.1, 82.04, 422/83, 98, 231, 305
See application file for complete search history.

(56) References Cited

U.S. PATENT DOCUMENTS

| | | | | |
|---|---|---|---|---|
| 2,912,367 A | * | 11/1959 | Asendorf et al. | 205/780.5 |
| 4,731,232 A | * | 3/1988 | Fischer et al. | 423/236 |
| 5,269,832 A | | 12/1993 | Meijer | |

FOREIGN PATENT DOCUMENTS

| | | | |
|---|---|---|---|
| DE | 275154 | * | 12/1987 |
| DE | 292324 | * | 2/1990 |
| WO | WO 95/33203 | * | 12/1995 |
| WO | WO 2007/137562 | * | 12/2007 |

* cited by examiner

*Primary Examiner* — Brian R Gordon
(74) *Attorney, Agent, or Firm* — Setter Roche LLP

(57) ABSTRACT

The invention relates to a method for continuously determining the concentration of at least one CN compound in an aqueous solution, wherein a carrier gas, for example compressed air, is introduced into the aqueous solution and the introduced carrier gas is fed at least partially to a gas analyzer, for example an HCN gas analyzer, the analysis data of which are considered in the determination of the concentration of the CN compound in the aqueous solution. In order to create advantageous method conditions, the temperature of the aqueous solution exposed to carrier gas is considered in the determination of the concentration of the CN compound.

12 Claims, 3 Drawing Sheets

METHOD FOR CONTINUOUSLY
DETERMINING THE CONCENTRATION OF
AT LEAST ONE CN COMPOUND IN AN
AQUEOUS SOLUTION

FIELD OF THE INVENTION

The invention relates to a method for continuously determining the concentration of at least one CN compound in an aqueous solution in which a carrier gas, for example compressed air, is introduced into the aqueous solution and at least part of the introduced carrier gas is conveyed to a gas analyzer, for example an HCN gas analyzer, whose analysis data are taken into account in the determination of the concentration of the CN compound in the aqueous solution.

BACKGROUND OF THE INVENTION

In order to detect cyanide compounds (CN compounds) in aqueous solutions, it is known from the prior art (DE102006026044A1) to first expel the CN compounds from the liquid phase into a gas phase and then to deduce the concentration of the CN compounds in the aqueous solution by using a gas sensor or gas analyzer to detect the expelled CN compounds, for example HCN. In order to expel the CN compounds, DE102006026044A1 proposes acting on the aqueous solution with a carrier gas. It also proposes using gas access determining equipment to detect the quantity of gas to be measured in order to thus achieve a precise measurement. Such equipment, however, is complex in design and results in a comparatively temperamental process. In addition, devices of this kind require a comparatively complex reactor with a temperature control device in order to ensure a controlled expulsion of the CN compounds and thus reproducible measurement results. Such reactors, however, do not permit rapid reaction to toxic solutions such as aqueous solutions with elevated concentrations of CN compounds; as a result of this, the method can in fact be used for verifying the concentration of CN compounds, but not for controlling a very rapid reaction chain.

In addition, it is known (DD 275 154 A3) to introduce a membrane module into an aqueous solution, with a carrier gas flowing through it, which is insulated in relation to the aqueous solution. Hydrocyanic acid can enter through the membrane module and, carried along by the carrier gas, can be subjected to a joint analysis. The above-cited reference also proposes taking into account the temperature of the aqueous solution for a measurement correction. A membrane module, however, is fairly susceptible to contamination so that it is not possible to guarantee a stable method and stable device. In addition, a general measurement of the temperature of an aqueous solution cannot enable achievement of a precise method.

The object of the invention, therefore, is to embody a method of the type described at the beginning so that it is possible not only to ensure a sufficiently precise determination of the concentration of CN compounds in an aqueous solution, but also to provide a continuous method. In addition, the method should be fast-reacting.

SUMMARY OF THE INVENTION

The invention attains the stated object in that the temperature of the aqueous solution that is acted on by the carrier gas is taken into account when determining the concentration of the CN compounds.

If the temperature of the aqueous solution that is acted on by the carrier gas is taken into account when determining the concentration of CN compounds, then it is possible to carry out a temperature measurement that is relevant for a measurement correction because the temperature taken into account is the temperature of the specific part of the solution that cooperates with the method for determining the concentration of CN compounds. It is thus also advantageously possible to achieve a fast-reacting method because by contrast with the prior art, the aqueous solution does not have to be brought to temperature before the expulsion of the CN compounds in order to be able to achieve a reproducible and exact calculation of the concentration of CN compounds. By taking into account the current and relevant temperature of the aqueous solution, namely of the part of the aqueous solution being acted on by the carrier gas, it is therefore possible to always ensure a high degree of precision because this special temperature detection makes it possible to adapt the parameters for deducing the concentration of CN compounds in the aqueous solution via the current analysis data of the gas analyzer. Complex gas access equipment, membrane modules, and other measures intended to increase the measurement precision are therefore unnecessary—because the carrier gas is simply introduced into the solution—which can yield not only a reduction in costs, but also a stable method due to its simplicity and ruggedness. The invention thus excels in comparison to the prior art not only by means of its stability, but also through the possibility it offers for continuously determining the CN concentration of aqueous solutions.

Simple method conditions in the determination of the CN concentration are achieved when a correction value that changes as a function of the temperature is taken into account. It is thus namely possible to use the current temperature to quickly supply an appropriate correction value for the method so that it is possible to ensure a precise method even with a low amount of computing effort.

The expulsion of the CN compound into a gas phase can be improved by injecting the carrier gas into the aqueous solution.

If a stabilizer such as CuSu is added to the aqueous solution, then the precision of the method can be improved by hindering the transition into a low-energy state.

In order to be able to reduce the influence of external disturbance variables, it is possible to act on the aqueous solution with carrier gas in a reactor that is sealed in a gas-tight fashion. This makes it possible not only to ensure a precise determination of the concentration of CN compounds, but also to simplify the design requirements for supplying the carrier gas to the gas sensor, making it possible to achieve an inexpensive method.

If the pH value of the aqueous solution is reduced, it is then possible to improve an expulsion of the CN compound by means of the carrier gas. For example, such a reduction can occur before or at the same time as the introduction of the carrier gas into the aqueous solution, for example by adding hydrochloric acid or by using carbonic acid to produce the carrier gas.

With regard to precise and reproducible method conditions, it turns out to be particularly advantageous if the pH value of the aqueous solution is set to less than four.

In order to carry out the method, a device is proposed in which the reactor has a temperature sensor that records the temperature of the aqueous solution and is connected to a computing unit for additionally taking into account the temperature of the aqueous solution in the determination of the concentration of the CN compound.

If the reactor has a temperature sensor that records the temperature of the aqueous solution and is connected to the computing unit, then when determining the concentration of the CN compound, it is easily possible to take into account specifically this temperature of the aqueous solution, which can be decisive for the precision of the method. It has specifically turned out that what is of particular importance for the measurement correction is not the general temperature of the aqueous solution, but the temperature of the part of the aqueous solution that is acted on with carrier gas. It is therefore possible to produce a device that is particularly precise and stable. In addition, it is possible to dispense with complex gas access equipment, membrane modules, and other measures, thus yielding a simple operation and an inexpensive device.

If the temperature sensor is provided at least in the vicinity of the aqueous solution that is acted on with carrier gas, then simple design requirements can yield a precise measurement. It is thus possible to avoid a complex deduction as to the relevant temperature when the sensor is positioned at another location of the aqueous solution.

BRIEF DESCRIPTION OF THE DRAWINGS

The figures show several exemplary embodiments of the subject of the invention.

DETAILED DESCRIPTION OF THE PREFERRED EMBODIMENTS

Figure 1:
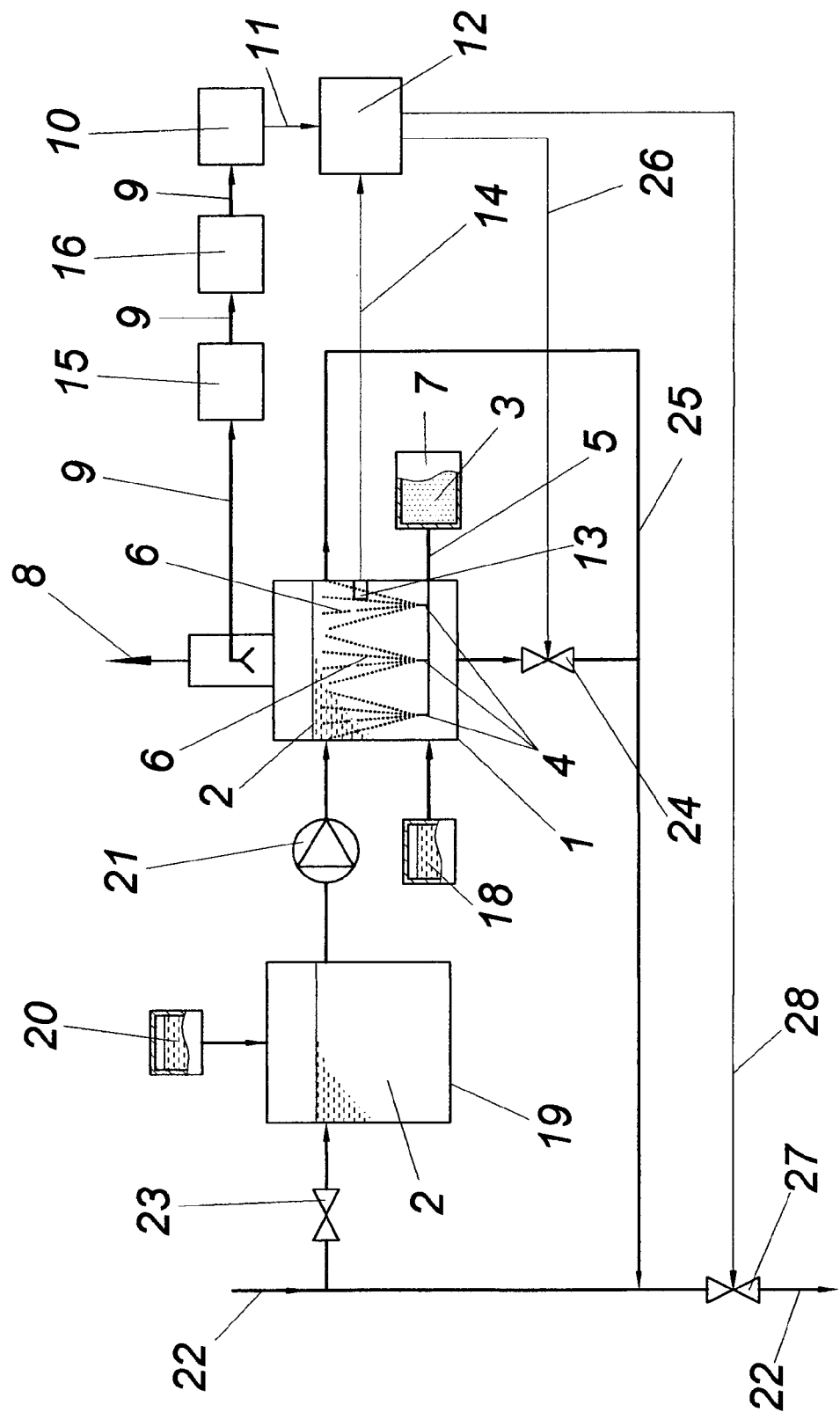
FIG. 1: is a schematic view of a first exemplary embodiment of a device according to the invention for carrying out the method.

The device according to the invention for carrying out the method shown by way of example in FIG. 1 has a reactor 1 in which an aqueous solution 2 is provided, which contains cyanide compounds (CN compounds) that are not depicted in detail. Nozzles 4 that are connected to a carrier gas line 5 introduce a carrier gas 3 into this aqueous solution 2 so that conical bubble formations 6 can be produced. The carrier gas 3 is stored in a carrier gas tank 7 that is connected to the carrier gas line 5 via a valve that is not shown in detail. The discharge air 8, which is produced in the reactor 1 and includes at least part of the introduced carrier gas 3, is supplied via a gas sampling line 9 to a gas analyzer 10 whose analysis data 11 are supplied to a computing unit 12 for computing the concentration of one CN compound and/or several CN compounds in the aqueous solution 2. In order to achieve an advantageous and in particular fast-reacting determination, according to the invention, the temperature of the aqueous solution 2 in the reactor 1 is taken into account in this determination. For this purpose, a temperature sensor 13 is provided in the tank 2, whose temperature data 14 are supplied to the computing unit 12. For example, this temperature sensor 13 is provided so that it can also measure the temperature of the solution 2 in the reactor 1 that is acted on by the carrier gas. According to FIG. 1, this temperature sensor 13 in the reactor 1 can be situated almost anywhere, but is advantageously situated in the region of the aqueous solution 2 that is acted on in order to thus be able to record exact temperature data 14 of this part of the aqueous solution 2. Based on the temperature data 14, it is possible to simply adapt and improve the continuity of the continuous results of the gas measurement on the one hand and the current concentration of the CN compound in the aqueous solution 2 on the other so that even with comparatively powerful temperature fluctuations in the supplied aqueous solution 2, a high degree of precision can be achieved in the determination process. In general, it is also conceivable to provide each nozzle 4 with its own temperature sensor 14 so as to detect the temperature of the aqueous solution 2 that is acted on by the respective nozzle, thus making it possible to improve the precision even further; this embodiment, however, has not been shown in the drawings.

Figure 3:
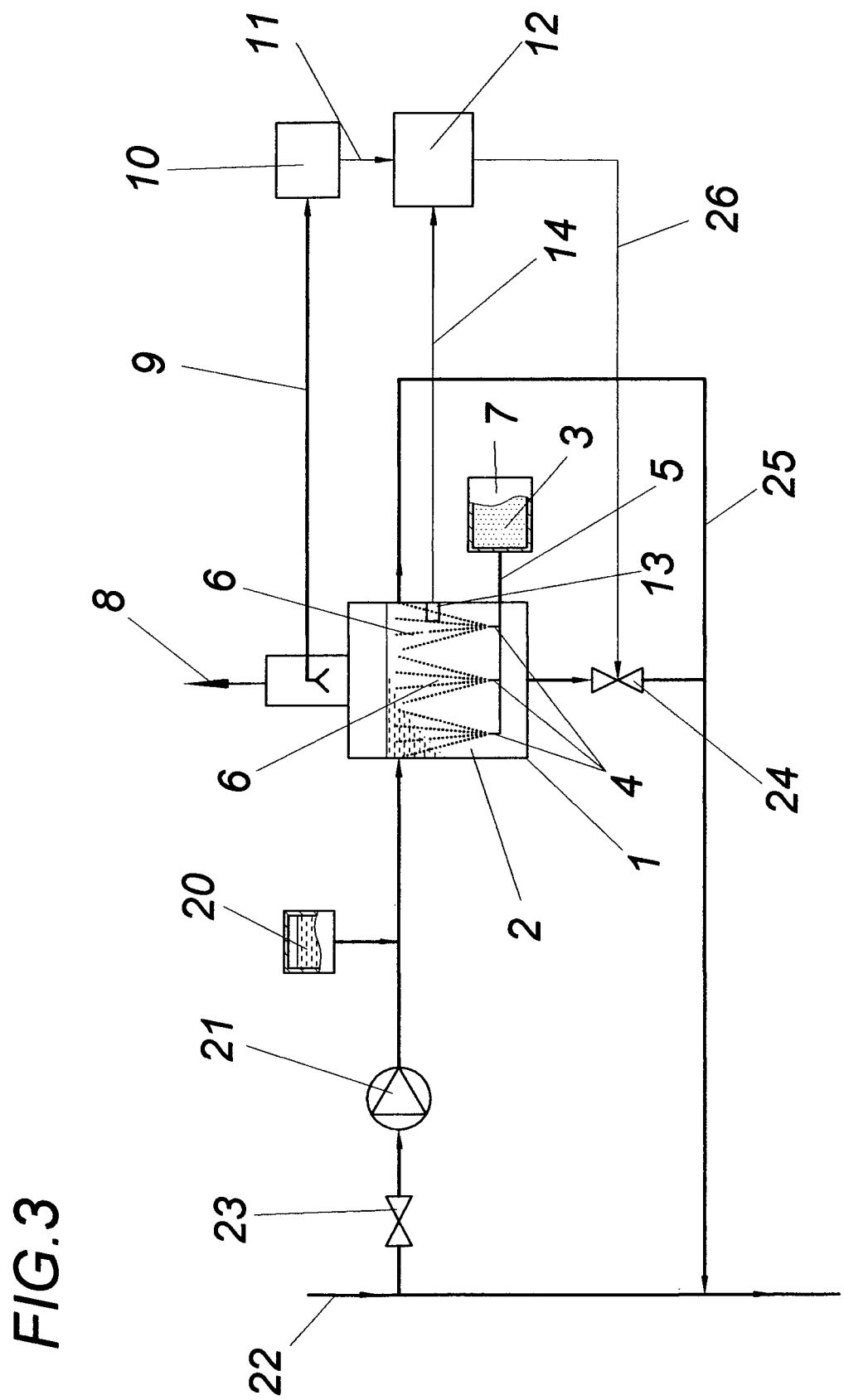
FIG. 3: shows a simplified second embodiment according to FIG. 1.

For example, HCN gas analyzers 10 have turned out to be particularly advantageous for measuring the HCN gases and/or their concentration in the supplied carrier gas 3, said HCN gases having been expelled from the aqueous solution. In order to improve the gas measurement, a gas cooler 15 can be provided in the gas sampling line 9 and possibly also a selective filter 16, which acts on H2S, SO2, and NO, for example, in order to thus reduce interfering influences on the gas analyzer 10. A sample gas pump, not shown in detail, can also possibly be provided upstream of the gas analyzer 10. According to FIG. 3, however, as shown in the exemplary embodiment, this can be entirely eliminated.

Figure 2:
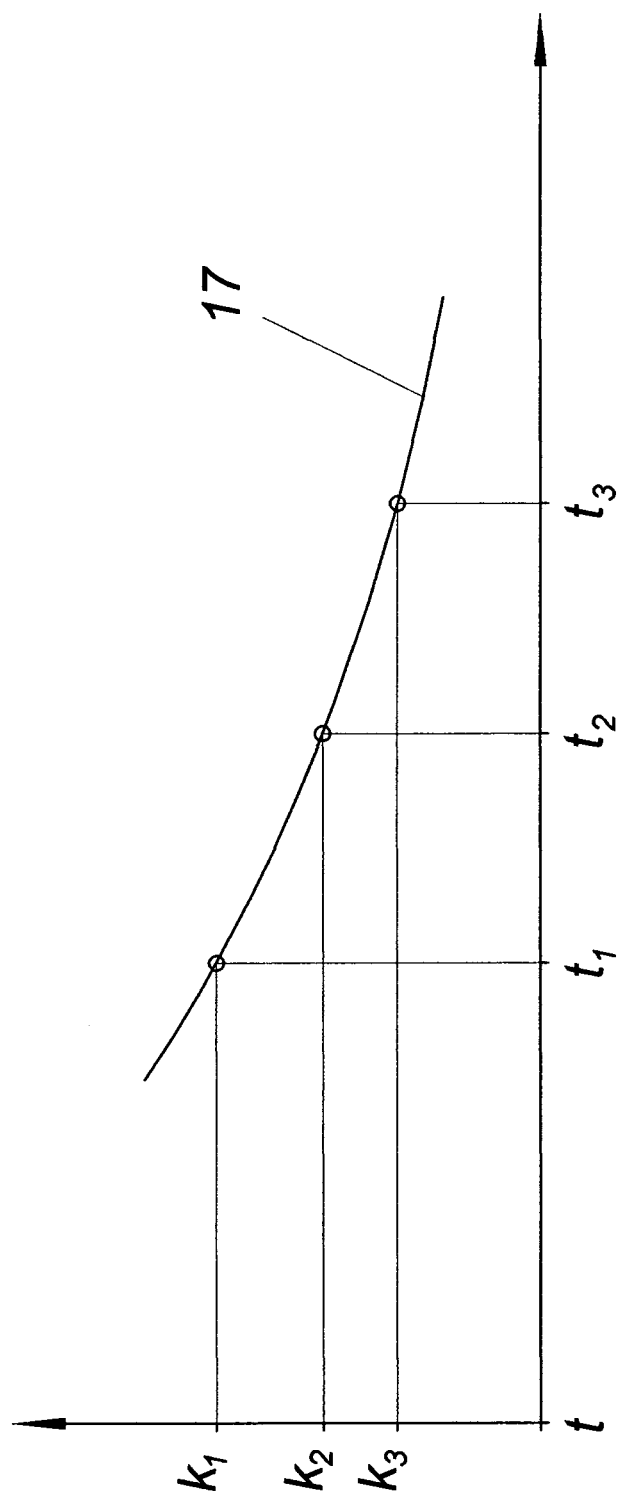
FIG. 2: shows a sample curve for a correction value as a function of the temperature of the aqueous solution.

A simple computation option is achieved if an altered correction value k1, k2, or k3 is taken into account depending on the respective temperature t1, t2, or t3 of the aqueous solution 2, which is more evident from FIG. 2. It is thus possible at a temperature t1 to simply determine or read off the correction value k1 from the correction value curve 17, said correction value curve 17 constituting an E-curve, for example.

To improve the precision of the method, a stabilizer 18 (such as CuSu) can be added to the aqueous solution 2 in the reactor, as shown in FIG. 1. The reactor 1 is advantageously embodied as gas-tight in order to thus avoid interfering influences.

Before the introduction of the carrier gas 3, the pH value of the aqueous solution 2 is lowered. For this purpose, hydrochloric acid 20 is added to the aqueous solution 2, which can take place in the line downstream of the pump 21 according to FIG. 3 or in a pretreatment tank 19 according to FIG. 1.

Advantageous method conditions are achieved if the pH value of the aqueous solution 2 is set to four or lower and/or is regulated in this regard before the aqueous solution 2 is supplied to the reactor 1. For the sake of simplicity, the regulation is not shown in detail. To achieve the pressure connection between the supply line 19 and the reactor 1, it is possible, for example, to provide a feed pump 21 that can also control a metered introduction of the aqueous solution 2.

The aqueous solution 2 to be analyzed can be drawn from the exhaust water line 22 via a valve 23 with the aid of the pump 21; after the analysis, the aqueous solution 2 can be conveyed from the reactor 1 via an outlet line 25 and fed into the exhaust water line 22, particularly in an unpressurized fashion.

In order to be able to cleanse the reactor 1 of any suspended solids, it is possible for the computing unit 12 to at least partially bleed the reactor 11 via an outlet valve 24 and thus to empty it via the outlet line 25 and the exhaust water line 22.

According to the invention, the fast-reacting method can open up the possibility of holding back toxic exhaust water or aqueous solutions 2 containing CN compounds before the contamination spreads to connected systems; these systems have not been shown in detail. For this purpose, a device embodied in the form of a valve 27 can be provided, for example in the exhaust water line 22, which can hold back the exhaust water as a function of the continuous determination of the concentration of at least one CN compound in an aqueous solution 2. For this purpose, a control line 28 is provided, via which the computing unit 12 can actuate the valve 27.

The invention claimed is:

1. A method for continuously determining the concentration of at least one CN compound in an aqueous solution comprising:

introducing a carrier gas through one or more nozzles into an aqueous solution in a reactor, thereby forming one or more bubble formations in the aqueous solution;

conveying at least part of the introduced carrier gas from the reactor to a gas analyzer, which analyzes a composition of the carrier gas for at least one CN compound;

in the reactor, using one or more temperature sensors positioned in at least one of the bubble formations in the aqueous solution to measure a temperature of the aqueous solution that is being acted on by the carrier gas; and using analysis data from the gas analyzer and the measured temperature of the aqueous solution acted on by the carrier gas to compute the concentration of the at least one CN compound in the aqueous solution.

2. The method as recited in claim 1, further comprising using an altered correction value that changes as a function of the temperature to more accurately compute the concentration of the at least one CN compound in the aqueous solution.

3. The method as recited in claim 1, comprising injecting the carrier gas into the aqueous solution in the reactor.

4. The method as recited in claim 1 further comprising adding a stabilizer to the aqueous solution.

5. The method as recited in claim 1, wherein the reactor is sealed in a gas-tight fashion.

6. The method as recited in claim 1, further comprising lowering a pH value of the aqueous solution.

7. The method as recited in claim 6, wherein the pH value of the aqueous solution is set to less than four.

8. The method as recited in claim 1, wherein the carrier gas is compressed air.

9. The method as recited in claim 1, wherein the gas analyzer is an HCN gas analyzer.

10. The method as recited m claim 6, comprising lowering the pH value of the aqueous solution by adding acid.

11. A device equipped with a gas analyzer, comprising;

a reactor that contains an aqueous solution and has a carrier gas line that feeds into the aqueous solution of the reactor through one or more nozzles in order to introduce carrier gas, thereby forming one or more bubble formations in the aqueous solution, and has a gas sampling line, which is connected at a location above the aqueous solution of the reactor and conveys at least part of the introduced carder gas to the gas analyzer for gas analysis;

a computing unit connected to the gas analyzer for continuously determining a concentration of at least one CN compound in the aqueous solution while taking into account analysis data of the gas analyzer; and a temperature sensor located in the reactor and positioned in at least one of the bubble formations in the aqueous solution, wherein the temperature sensor records a temperature of the aqueous solution that is being acted on by the carrier gas and is connected to the computing unit in order to also take into account the temperature of the aqueous solution that is being acted on by the carder gas when determining the concentration of the CN compound.

12. The device as recited in claim 11, wherein the gas analyzer is an HCN gas analyzer.

* * * * *